US011246857B2

(12) United States Patent
Bosch et al.

(10) Patent No.: US 11,246,857 B2
(45) Date of Patent: Feb. 15, 2022

(54) ANTI-FUNGAL INHIBITORS

(71) Applicant: THE JOHNS HOPKINS UNIVERSITY, Baltimore, MD (US)

(72) Inventors: Jürgen Bosch, Pikesville, MD (US); Arturo Casadevall, Baltimore, MD (US); Eric H. Jung, Baltimore, MD (US)

(*) Notice: Subject to any disclaimer, the term of this patent is extended or adjusted under 35 U.S.C. 154(b) by 38 days.

(21) Appl. No.: 16/954,004

(22) PCT Filed: Dec. 12, 2018

(86) PCT No.: PCT/US2018/065062
§ 371 (c)(1),
(2) Date: Jun. 15, 2020

(87) PCT Pub. No.: WO2019/118527
PCT Pub. Date: Jun. 20, 2019

(65) Prior Publication Data
US 2021/0077464 A1    Mar. 18, 2021

Related U.S. Application Data

(60) Provisional application No. 62/598,633, filed on Dec. 14, 2017.

(51) Int. Cl.
*A61K 31/4184* (2006.01)
*A61P 33/06* (2006.01)
(Continued)

(52) U.S. Cl.
CPC ........ *A61K 31/4184* (2013.01); *A61K 9/0014* (2013.01); *A61K 31/167* (2013.01);
(Continued)

(58) Field of Classification Search
CPC .............. A61K 2300/00; A61K 31/167; A61K 31/403; A61K 31/4174; A61K 31/4184;
(Continued)

(56) References Cited

U.S. PATENT DOCUMENTS 5,339,363 A    8/1994  Fosgate
5,466,468 A    11/1995 Schneider et al.
(Continued)

FOREIGN PATENT DOCUMENTS

RU      2396955 C2     8/2012
WO   2014020152 A2     2/2014
WO   2015164850 A1    10/2015

OTHER PUBLICATIONS

Jung et al. (American Society for Microbiology, vol. 3, Issue 2, Apr. 2018, pp. 1-12).*

(Continued)

*Primary Examiner* — Savitha M Rao
(74) *Attorney, Agent, or Firm* — Casimir Jones, S.C.; Jeffrey W. Childers

(57) ABSTRACT

Described herein are methods of treating or preventing a fungal infection by administering one or more compounds of the present invention to a subject. The methods of the present invention treat or prevent a fungal infection of *C. neoformans*, *C. gattii*, *L. prolificans*, *C. albicans*, or a combination thereof, as examples. The compounds of the present invention may be administered to a subject with other agents such as antifungal agents.

12 Claims, 10 Drawing Sheets

(51) Int. Cl.

| | |
|---|---|
| A61P 31/10 | (2006.01) |
| A61K 9/00 | (2006.01) |
| A61K 31/167 | (2006.01) |
| A61K 31/403 | (2006.01) |
| A61K 31/4196 | (2006.01) |
| A61K 38/17 | (2006.01) |
| A61K 39/395 | (2006.01) |
| A61K 45/06 | (2006.01) |
| C07K 14/47 | (2006.01) |
| C07K 14/705 | (2006.01) |
| C07K 16/18 | (2006.01) |

(52) U.S. Cl.
CPC ........ *A61K 31/403* (2013.01); *A61K 31/4196* (2013.01); *A61K 38/17* (2013.01); *A61K 38/1787* (2013.01); *A61K 39/3955* (2013.01); *A61K 45/06* (2013.01); *A61P 31/10* (2018.01); *A61P 33/06* (2018.01); *C07K 14/47* (2013.01); *C07K 14/70571* (2013.01); *C07K 16/18* (2013.01); *C07K 2317/622* (2013.01); *C07K 2319/33* (2013.01)

(58) Field of Classification Search
CPC .............. A61K 31/4196; A61K 31/496; A61K 31/506; A61K 31/513; A61K 31/7048; A61K 38/17; A61K 38/1787; A61K 39/3955; A61K 45/06; A61K 9/0014; A61P 31/10; A61P 33/06; C07K 14/47; C07K 14/70571; C07K 16/18; C07K 2317/622; C07K 2319/33
See application file for complete search history.

(56) References Cited

U.S. PATENT DOCUMENTS

| | | | |
|---|---|---|---|
| 5,543,158 | A | 8/1996 | Gref et al. |
| 5,580,579 | A | 12/1996 | Ruddy et al. |
| 5,629,001 | A | 5/1997 | Michael et al. |
| 5,641,515 | A | 6/1997 | Ramtoola |
| 5,725,871 | A | 3/1998 | Ilium |
| 5,756,353 | A | 5/1998 | Debs |
| 5,780,045 | A | 7/1998 | McQuinn et al. |
| 5,792,451 | A | 8/1998 | Sarubbi et al. |
| 5,804,212 | A | 9/1998 | Ilium |
| 6,613,308 | B2 | 9/2003 | Bartus et al. |
| 2011/0230451 | A1 | 9/2011 | Lorsch et al. |
| 2012/0122872 | A1 | 5/2012 | Krysan et al. |

OTHER PUBLICATIONS

Wilson, et al., The direct cost and incidence of systemic fungal infections. Value Health. Jan.-Feb. 2002;5(1):26-34.
Castelli, M., et al., "Novel antifungal agents: a patent review (2013-present)" Expert Opinion on Therapeutic Patents, 2017, vol. 27, No. 4, 415-426.
Pfaller, et al., Epidemiology of invasive candidiasis: a persistent public health problem. Clin Microbiol Rev. Jan. 2007;20(1):133-63.
Rajasingham, et al., Global burden of disease of HIV-associated cryptococcal meningitis: an updated analysis Lancet Infect Dis. Aug. 2017;17(8):873-881.
Park, et al., Estimation of the current global burden of cryptococcal meningitis among persons living with HIV/AIDS. Feb. 2, 2009;23(4):525-30.
Galanis, et al., Epidemiology of Cryptococcus gattii, British Columbia, Canada, 1999-2007. Emerg Infect Dis. Feb. 2010;16(2):251-257.
Harris, et al., Cryptococcus gattii in the United States: clinical aspects of infection with an emerging pathogen. Clin Infect Dis. Dec. 2011;53(12):1188-95.
Pappas, Cryptococcal infections in non-HIV-infected patients. Trans Am Clin Climatol Assoc. 2013;124:61-79.
Gast, et al., Azole Resistance in Cryptococcus gattii from the Pacific Northwest: Investigation of the Role of ERG11. Antimicrob Agents Chemother. Nov. 2013;57(11):5478-5485.
Gutch, et al., Antifungal susceptibility of clinical and environmental Cryptococcus neoformans and Cryptococcus gattii isolates in Jabalpur, a city of Madhya Pradesh in Central India. Braz J Microbiol Oct.-Dec. 2015;46(4):1125-1133.
Rodriguez_Tudela, et al., Epidemiology and outcome of Scedosporium prolificans infection, a review of 162 cases. Med Mycol. Jun. 2009;47(4):359-70.
Cortez, et al., Infections caused by *Scedosporium* spp. Clin Microbiol Rev. Jan. 2008;21(1):157-197.
Cuenca-Estrella, et al., Comparative in-vitro activity of voriconazole (UK-109,496) and six other antifungal agents against clinical isolates of Scedosporium prolificans and Scedosporium apiospermum. J Antimicrob Chemother. Jan. 1999;43(1):149-51.
Tortorano, et al., ESCMID and ECMM joint guidelines on diagnosis and management of hyalohyphomycosis *Fusarium* spp., *Scedosporium* spp. and others Clin Microbiol Infect. Apr. 2014;20 Suppl 3:27-46.
Zapotoczna, M., et al., "Novel anti-staphylococcal and anti-biofilm properties of two anti-malarial compounds: MMV665953 {1-(3-chloro-4-fluorophenyl)-3-(3,4-dichlorophenyl)urea} and MMV665807 {5-chloro-2-hydroxy-N-[3-(trifluoromethyl)phenyl]benzamide}" Journal of Medical Microbiology 2017;66:377-387.
Jackson, et al., A phase II randomized controlled trial adding oral flucytosine to high-dose fluconazole, with short-course amphotericin B, for cryptococcal meningitis. AIDS. Jul. 17, 2012;26(11):1363-70.
Shields, et al., Clinical perspectives on echinocandin resistance among *Candida* species. Curr Opin Infect Dis. Dec. 2015;28(6):514-22.
Smith, et al., Increased Antifungal Drug Resistance in Clinical Isolates of Cryptococcus neoformans in Uganda. Antimicrob Agents Chemother. Dec. 2015;59(12):7197-7204.
Gamo, et al., Thousands of chemical starting points for antimalarial lead identification. Nature. May 20, 2010;465(7296):305-10.
Spangenberg, et al., The open access malaria box: a drug discovery catalyst for neglected diseases. PLoS One. Jun. 17, 2013;8(6):e62906.
Van Voorhis, et al., Open Source Drug Discovery with the Malaria Box Compound Collection for Neglected Diseases and Beyond. PLoS Pathog. Jul. 28, 2016;12(7):e1005763.
Janbon, et al., Analysis of the genome and transcriptome of *Cryptococcus neoformans* var. *grubii* reveals complex RNA expression and microevolution leading to virulence attenuation. PLoS Genet. Apr. 17, 2014;10(4)e1004261.
D'Souza, et al., Genome variation in Cryptococcus gattii, an emerging pathogen of immunocompetent hosts. MBio. Feb. 8, 2011;2(1):e00342-10.
Farrer, et al., Genome Evolution and Innovation across the Four Major Lineages of Cryptococcus gattii. MBio. Sep. 1, 2015;6(5):e00868-15.
Wood, et al., Clinical features of human infection with Scedosporium inflatum. Clin Infect Dis. May 1992;14(5):1027-1033.
Jones, et al., The diploid genome sequence of Candida albicans. Proc Natl Acad Sci USA. May 11, 2004;101(19):7329-34.
Casadevall, et al., Characterization of a murine monoclonal antibody to Cryptococcus neoformans polysaccharide that is a candidate for human therapeutic studies. Antimicrob Agents Chemother. Jun. 1998;42(6):1437-46.
Hain, et al., Virtual Screening and Experimental Validation Identify Novel Inhibitors of the Plasmodium falciparum Atg8-Atg3 Protein-Protein Interaction. ChemMedChem. Apr. 19, 2016;11(8):900-10.
Hain, et al., Identification of an Atg8-Atg3 protein-protein interaction inhibitor from the medicines for Malaria Venture Malaria Box active in blood and liver stage *Plasmodium falciparum* parasites. J Med Chem. Jun. 12, 2014;57(11):4521-31.
Wang, et al.. Cryptococcus neoformans melanin and virulence: mechanism of action. Infect Immun. Aug. 1995; 63(8):3131-3136.
Cox, et al., Urease as a virulence factor in experimental cryptococcosis. Infect Immun. Feb. 2000;68(2):443-8.

(56) References Cited

OTHER PUBLICATIONS

Kratky, et al., Antifungal Activity of Salicylanilides and Their Esters with 4-(Trifluoromethyl)benzoic Acid. Molecules. Aug. 7, 2012;17(8):9426-42.

Kratky, et al., In vitro antibacterial and antifungal activity of salicylanilide pyrazine-2-carboxylates. Med Chem. Jul. 2012;8(4):732-41.

* cited by examiner

ANTI-FUNGAL INHIBITORS

CROSS-REFERENCE TO RELATED APPLICATIONS

This application is a 35 U.S.C. § 371 U.S. national entry of International Application PCT/US2018/065062, having an international filing date of Dec. 12, 2018, which claims the benefit of U.S. Provisional Application No. 62/598,633, filed Dec. 14, 2017, the content of each of the aforementioned applications is herein incorporated by reference in their entirety.

STATEMENT OF GOVERNMENTAL INTEREST

This invention was made with government support under grant number AI033142, awarded by the National Institutes of Health. The government has certain rights in the invention.

BACKGROUND OF THE INVENTION

The estimated global burden of fungal diseases is an ongoing problem, especially in developing and rural regions where thorough diagnostics and treatment are difficult to distribute. The distribution and availability of the drugs currently available to treat potentially life threatening fungal diseases is inefficient and costly. A study in 2002 projected an average incidence of fungal infection at 306 per million US population estimating a total direct cost of $2.6 billion and an average of $31,200 per patient. When this data is transposed onto the areas of the highest affected population in sub-Saharan Africa, where the average annual income per capita is approximately $750, the cost for treatment is generally unattainable.

Candidiasis and cryptococcosis are two widespread human mycoses, caused by ascomycetous *Candida* spp. and basidiomycetous *Cryptococcus* spp., respectively. *Candida* spp. are found in the commensal flora and can cause a diverse set of diseases in humans ranging from mucosal to systemic involvement, the most common being *Candida albicans*. The disease most commonly associated with *Candida* spp. is oropharyngeal candidiasis or thrush, though occasionally other mucosal linings such as the vaginal wall occur. In some circumstances, such as the breakage of mucosa or immunosuppression, a relatively benign or self-limited candidiasis can transform into an invasive pathogen which can disseminate causing candidemia, meningitis or deep organ disease with high fungal burden. *Cryptococcus neoformans* is a facultative intracellular pathogen that is now associated with the highest worldwide mortality amongst HIV/AIDS patients, resulting in 180,000 deaths per annum, predominantly in Sub-Saharan Africa. Infection occurs via inhalation of spores and is controlled by alveolar macrophages phagocytosing the pathogen. In immunocompetent individuals, *C. neoformans* inhalation leads to a latent infection, cleared or eventually sequestered to the lung in the form of granulomatous inflammation. However, in immunocompromised individuals, such as HIV/AIDS patients or organ transplant recipients on immunosuppressive regimen, the localized infection of the lung can disseminate to the central nervous system. Cryptococcosis is comprised of pneumonia and meningoencephalitis, acute swelling of the brain and meninges, and cryptococcomas, small tumor-like masses of infection, both of which can subsequently lead to an intracranial buildup in pressure. *Cryptococcus gattii* is a related species, however far rarer as only 218 cases were reported in British Columbia, Canada during 1999-2007 and 96 cases reported in the Pacific Northwest of the US during 2004-2011. *C. gattii* is most known for emerging in 1999 on Vancouver Island, British Columbia, Canada before spreading to the Pacific Northwest of the United States. Wild and domestic animal populations as well as healthy individuals developed life threatening cryptococcosis. While *C. neoformans* normally affects immunocompromised individuals, the hallmark characteristic of *C. gattii* is the ability to cause disease and in healthy, immunocompetent individuals. *C. gattii* is also known for having natural resistance to the typical azoles used in the treatment of cryptococcosis.

*Lomentospora prolificans*, formerly *Scedosporium prolificans*, is found worldwide and is a highly antifungal resistant dermatiaceous mold related to *Scedosporium apiospermum*. *L. prolificans* is an opportunistic emerging pathogen found in the developed and developing world, fatal chiefly among the immunocompromised although infection in the immunocompetent can still lead to subcutaneous infections causing debilitating disease in skin, soft tissue and bone (mycetoma) infections. The most notable characteristic of *L. prolificans* is the intrinsic antifungal resistance to common antifungal drugs such as amphotericin B, flucytosine, fluconazole, itraconazole, ketoconazole, miconazole and voriconazole. Clinical manifestation of *L. prolificans* can begin as a localized lesion from trauma or inhalation which can disseminate into systemic infection due to its capacity to spawn conidia in bodily fluids. Current treatment for *L. prolificans* infection is surgical debridement of affected tissue along with systemic high-dose antifungal therapy.

While significant strides have been made in the treatment of these fungal diseases, the administration of lifesaving antifungal therapies are difficult to manage. Amphotericin B, flucytosine and fluconazole are currently the default antifungal agents used to treat invasive fungal disease. Amphotericin B is administered intravenously and binds ergosterol in the fungal cell membrane causing leakage, however amphotericin B can have severe and sometimes lethal side effects. Flucytosine is administered orally and interferes with fungal RNA biosynthesis. Most therapeutic regiments require high dose fluconazole, which is administered orally or intravenously where it prevents ergosterol synthesis thereby disrupting the fungal cell membrane. While clinical studies have shown that triple combinations of the drugs are considered safe and effective, the aforementioned distribution and administration and clinical management of these long courses of treatment have proven extremely difficult, especially in regions where the need is most dire. Given the rise of antifungal resistant fungal clinical isolates of a diverse set of fungal species, there is a need for novel antifungal therapeutics with high fungicidal activity, low mammalian toxicity, oral bioavailability and cost effectivity.

SUMMARY OF THE INVENTION

One embodiment of the present invention is a method of treating or preventing a fungal infection in a subject comprising the steps of: administering a compound of Formula 1 to a subject having or suspected of having a fungal infection wherein the compound of Formula 1 is:

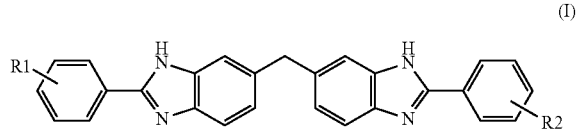

(I)

R1 is H,

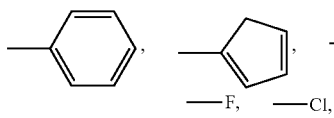, 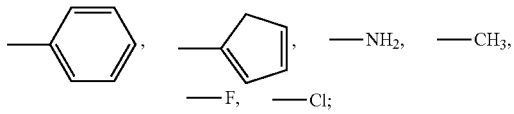

and R2 is H,

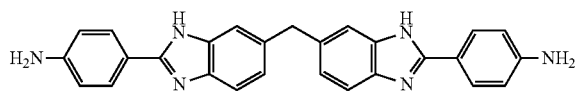

or a pharmaceutically acceptable salt, solvate, or stereoisomer thereof; and treating or preventing the fungal infection of the subject. The treatment or prevention of a fungal infection begins with providing a compound of Formula 1 to a subject, such as a human, that results in the growth of the fungal infection in the subject being less than the growth of a fungal infection in a reference subject not administered the compound of Formula I. Any method of administration of the compounds of the present invention to subjects may be used including oral, topical, or injection, as examples. The compound of Formula I may be administered to a subject with other agents such as an antifungal agents, for example. Examples of antifungal agents includes amphotericin B, flucytosine, fluconazole, itraconazole, ketoconazole, miconazole and voriconazole, or a combination thereof. The methods of the present invention may treat or prevent a fungal infection of *C. neoformans, C. gattii, L. prolificans, C. albicans*, or a combination thereof, as examples. One of the preferred compounds to be used in the present invention of Formula 1 is

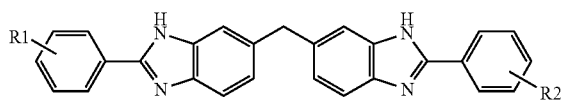

Another embodiment of the present invention is a method of treating or preventing a fungal infection in a subject, such as a human, comprising the steps of: administering a compound of Formula I, Formula II, Formula III, or a combination thereof to a subject having or suspected of having a fungal infection wherein Formula I is

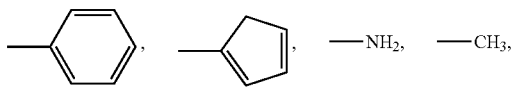

R1 is H,

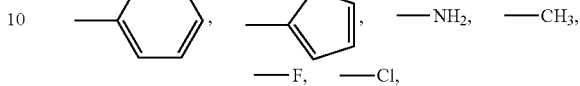

and
R2 is H.

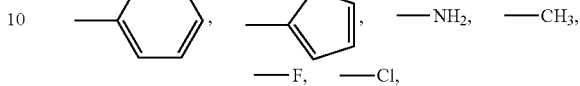

or a pharmaceutically acceptable salt, solvate, or stereoisomer thereof; wherein Formula II is

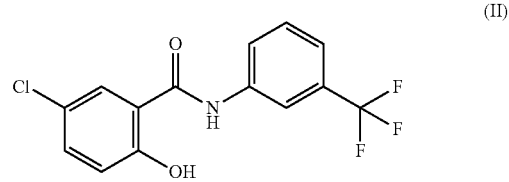 [SMILES: O=C(Nc1cccc(C(F)(F)F)c1)c1cc(Cl)ccc1O]

or a pharmaceutically acceptable salt, solvate, or stereoisomer thereof; wherein Formula III is

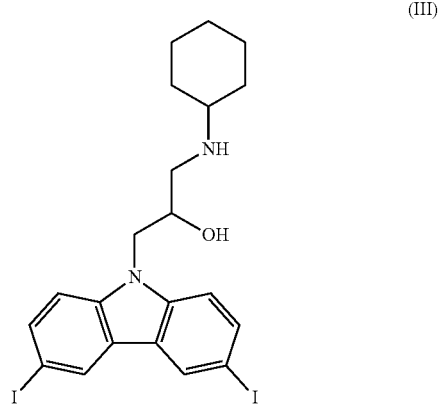 [SMILES: OC(CNC1CCCCC1)Cn1c2ccc(I)cc2c2cc(I)ccc21]

or a pharmaceutically acceptable salt, solvate, or stereoisomer thereof; and treating or preventing the fungal infection of the subject. Administering the compounds of Formula (I), (II), (III) or a combination thereof to a subject results in the growth of the fungal infection in the subject being less than the growth of a fungal infection in a reference subject not administered the compound of Formula I, Formula II, Formula III, or a combination thereof. Pharmaceutical compositions of the present invention may include a compound of Formula I, Formula II, Formula III or a combination thereof. A compound of Formulas (I), (II), (III) or a combination thereof may be administered to a subject with other agents such as an antifungal agents, for example. Examples of antifungal agents includes amphotericin B, flucytosine, fluconazole, itraconazole, ketoconazole, miconazole and voriconazole, or a combination thereof. The methods of the present invention may treat or prevent a fungal infection of *C. neoformans, C. gattii, L. prolificans, C. albicans*, or a combination thereof, as examples.

In accordance with an embodiment, the present invention provides a compound of formula I:

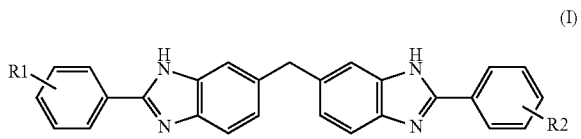

R1 is H,

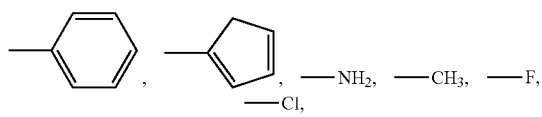

and
R2 is H,

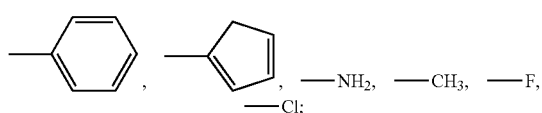

or a pharmaceutically acceptable salt, solvate, or stereoisomer thereof; and treating or preventing the fungal infection of the subject.

In accordance with an embodiment, the present invention provides a compound of formula II:

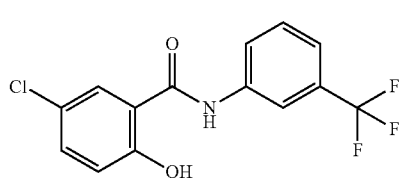 [SMILES: O=C(Nc1cccc(C(F)(F)F)c1)c1cc(Cl)ccc1O]

In accordance with an embodiment, the present invention provides a compound of formula III:

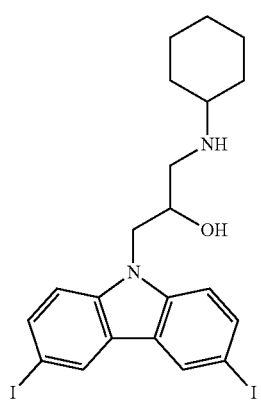

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a process such as autophagy as detected by methods such as those described herein. As used herein, an alteration includes a 10% change, preferably a 25% change, more preferably a 40% change, and most preferably a 50% or greater change."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "disease" is meant any condition or disorder that damages or interferes with the normal function of a cell, tissue, or organ. Examples of a disease is a fungal infection.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term, "obtaining" as in "obtaining an agent" includes synthesizing, purchasing, or otherwise acquiring the agent.

By "reduces" is meant a negative alteration of at least 10%, 25%, 50%, 75%, or 100%.

A "reference" refers to a standard or control conditions such as a sample (human cells) or a subject that is a free, or substantially free, of an agent such as one or more antifungal compositions of the present invention.

As used herein, the term "sensitivity" is the percentage of subjects with a particular disease.

As used herein, the term "specificity" is the percentage of subjects correctly identified as having a particular disease i.e., normal or healthy subjects. For example, the specificity is calculated as the number of subjects with a particular disease as compared to non-cancer subjects (e.g., normal healthy subjects).

By "specifically binds" is meant a compound or antibody that recognizes and binds a polypeptide of the invention, but which does not substantially recognize and bind other molecules in a sample, for example, a biological sample, which naturally includes a polypeptide of the invention.

As used herein, the term "subject" is intended to refer to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

(A) The mean size distribution of DM262 treated *C. neoformans* samples was analyzed using the brightfield information acquired on the ImageStream. Each sample contained >10000 single cells. No significant change is size is apparent between treated and control samples.

(B) Apoptotic index as determined based on morphology analysis by IDEAS 6.2 of DM262 treated *C. neoformans*.

DETAILED DESCRIPTION OF THE INVENTION

In 2010, Gamo et al. at GlaxoSmithKline (GSK) screened approximately 2 million compounds for antimalarial leads. They discovered 13,533 compounds that inhibited growth by more than 80% at 2 μM concentration in *Plasmodium falciparum*, the *Plasmodium* species associated with the highest malaria-related mortality. A subset of these compounds was made available to interested users in the form of the Medicines for Malaria Venture (MMV) Malaria Box. The compounds were selected to be chemically diverse and cover most scaffolds that inhibited growth of *Plasmodium* parasites. Since the distribution of these compounds, multiple research labs have performed drug screening on various human pathogens.

The inventors of the present invention screened the open source MMV Malaria Box compound library for potentially novel antifungal compounds. The inventors identified five compounds with antifungal activity before further screening additional dilutions in *C. neoformans*. The most promising compound MMV665943, herein referred to as DM262, was then synthesized de novo prior to screening in primary mammalian cells and both antifungal resistant and susceptible fungal species: *C. neoformans, C. gattii, L. prolificans* and *C. albicans*.

Figure 1A:
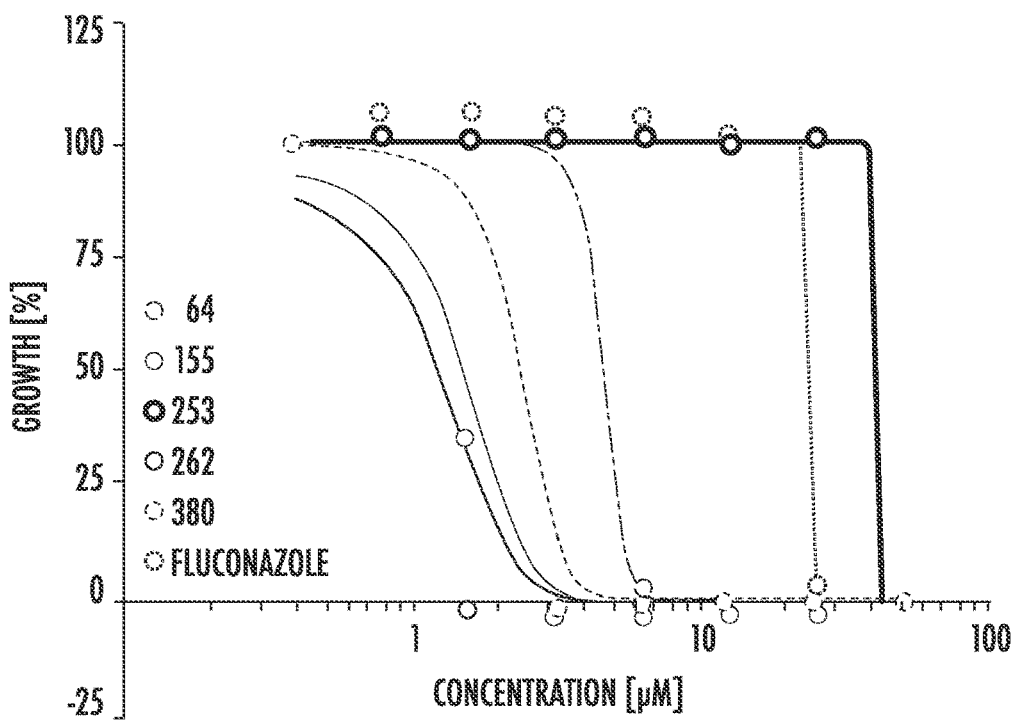
FIG. 1A-1B. Primary screening results of the Malaria Box MMV Library. A) Dose-response curve of selected compounds. *C. neoformans* cultures were plated and exposed to DMSO vehicle control or inhibitors for 72 h ranging from 0.39 μM-50 μM concentration. A parent molecule, PTA-DO (28, 29), of our 240-derivative library was included in the initial screen. B) After treatment, the liquid cultures were plated on Sabouraud rich media and grown at 30° C. to allow full recovery.
Figure 1B:
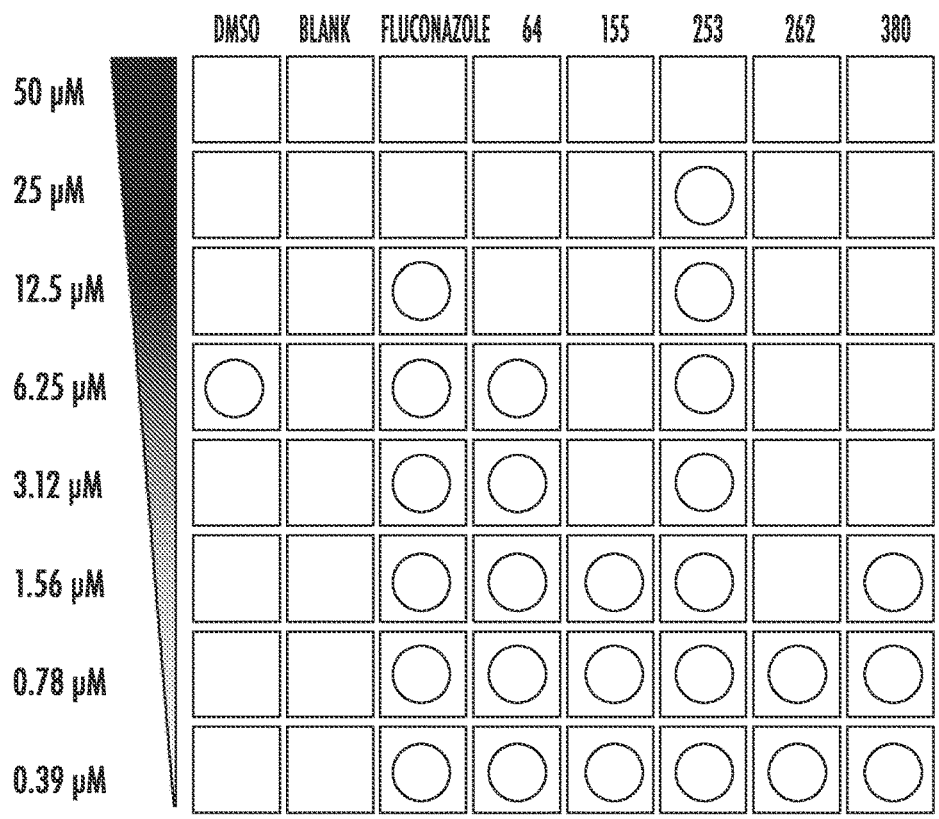
Figure 2A:
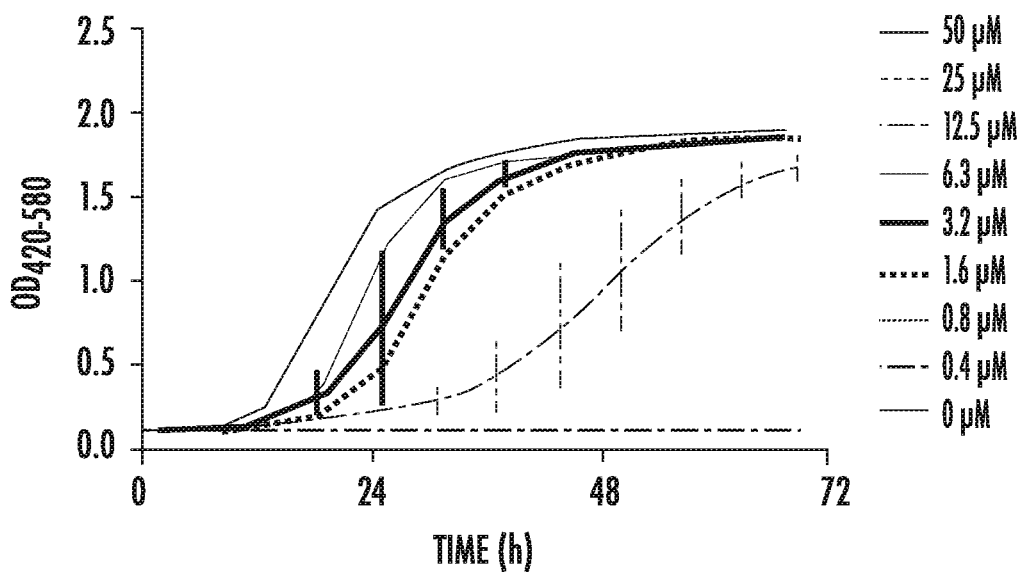
FIG. 2A-H. Dose dependent growth inhibition assays of fluconazole and DM262. A two-fold dilution series of fluconazole and DM262 in DMSO treatment in a variety of pathogenic fungal species. OD was measured in wideband (420-580 nm) to measure turbidity while accounting for differences in media color. The difference in growth inhibition between fluconazole is shown in *Cryptococcus neoformans* (A and B), *Lomentospora prolificans* (C and D), *Cryptococcus gattii* (E and F) and *Candida albicans* (G and H).
Figure 2B:
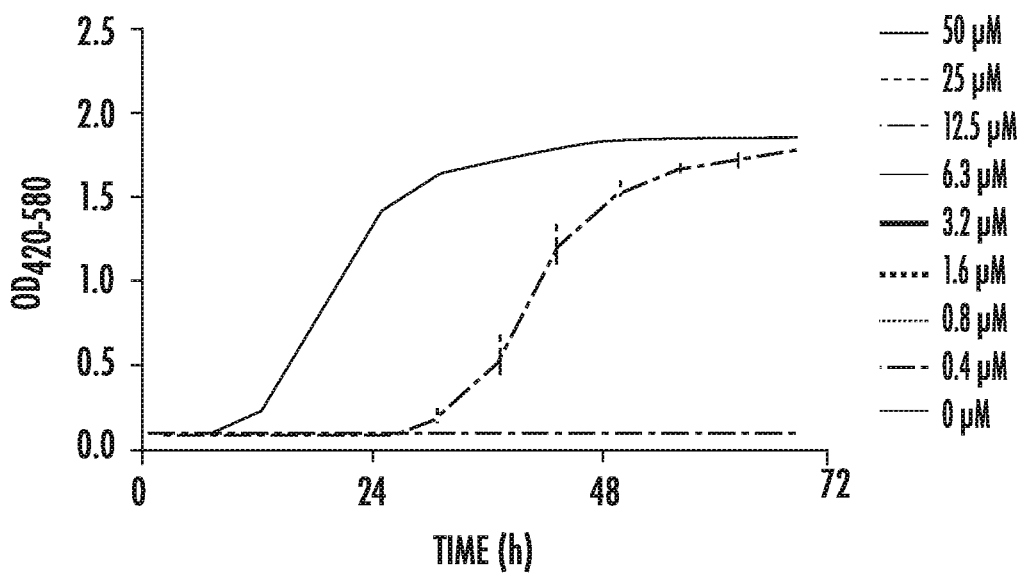

Primary screen and dose-response of selected candidates. To identify antifungal candidates in the MMV Malaria Box, the inventors initially casted the widest possible net. Growth inhibition assays were done using the Bioscreen C™ with constant agitation, in rich media and physiological relevant temperature of 37° to test the 400 antimalarial compounds against *C. neoformans*. The inventors identified 56 compounds that inhibited *C. neoformans* (FIG. 1C) at 50 µM final concentration. To further narrow down our candidate compounds, the inventors repeated growth inhibition assays on their 56 candidates in 2-fold dilution series for their dose-dependent activity. Five were selected based on their fungicidal activity relative to fluconazole, which is a commonly used antifungal drug against *C. neoformans* (FIG. 2A and Table 1). To examine whether or not each dose was fungicidal or just fungistatic, the inventors plated a sample of each dilution after 72 hours. They were allowed to grow at the optimal growth temperature of 30° for 24 hours on Sabouraud rich agar plates and colonies were examined for growth. MMV665943 (DM262) was the most effective compound, showing fungicidal activity down to 1.56 µM and fungistatic activity down to 0.8 µM, 16- and 32-fold more effective than fluconazole against *C. neoformans* (FIGS. 2A and B). Compounds MMV665807 (155) and MMV665882 (380) were equally effective showing fungicidal activity at 3.12 µM, still 8-fold more effective than fluconazole. MMV007374 (64) and MMV666079 (253) were assessed, however their low activity as well as 155 and 380 dissuaded us from further pursuit (FIG. 1B). To assess the fungicidal activity in other species, the inventors needed to synthesize more MMV665943, further referred to as DM262.

Table 1: Identified and validated antifungal compounds from the MMV Malaria Box library with fungicidal activity comparable or better than fluconazole.

XlogP values are derived from PubChem and describe the lipophilicity of the molecule. The topological polar surface area (tPSA) is a metric for predicting cell penetration, with values <140 to be favorable. The MIC was determined after 72 h drug exposure in liquid culture and continued growing on YPD-agar plates overnight for recovery of the cultures. Toxicity against human fibroblast was used to calculate the therapeutic index TI.

| ID | Molecular weight [Da] | XlogP | tPSA [Å$^2$] | Formula | Lipinski | MIC [µg/ml] | Toxicity human fibroblast [µM] | TI |
|---|---|---|---|---|---|---|---|---|
| Fluconazole | 306.27 | 0.4 | 81.6 | | ✓ | 7.6 | nd | nd |
| 64 | 267.3 | 3.8 | 66 | | ✓ | 1.6 | >32 | >5.3 |
| 155 | 315.7 | 4.5 | 49.3 | | ✓ | 0.5 | 0.024 | 0.02 |
| 253 | 287.3 | 4.5 | 51.8 | | ✓ | 7.2 | 11.4 | 0.5 |
| 262 | 430.5 | 4.9 | 109 | | ✓ | 0.3 | 11.4 | 16.4 |

| ID | Molecular weight [Da] | XlogP | tPSA [Å$^2$] | Formula | Lipinski | MIC [µg/ml] | Toxicity human fibroblast [µM] | TI |
|---|---|---|---|---|---|---|---|---|
| 380 | 574.2 | 5.3 | 37.2 | (cyclohexyl-NH-CH2-CH(OH)-CH2-N-(3,6-dimethylcarbazole)) | (✓) | 0.9 | 4.03 | 2.6 |

Figure 2C:
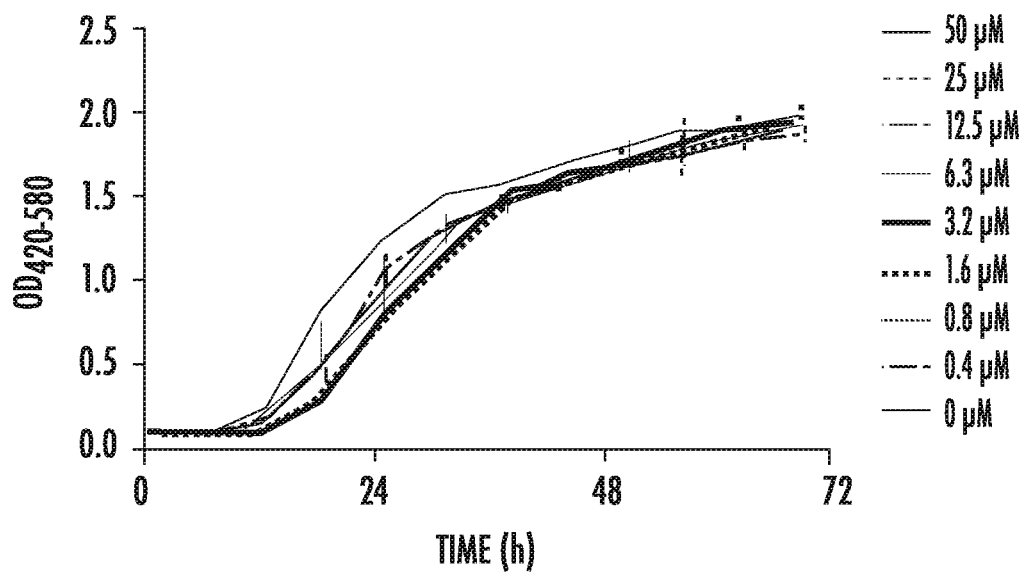
Figure 2D:
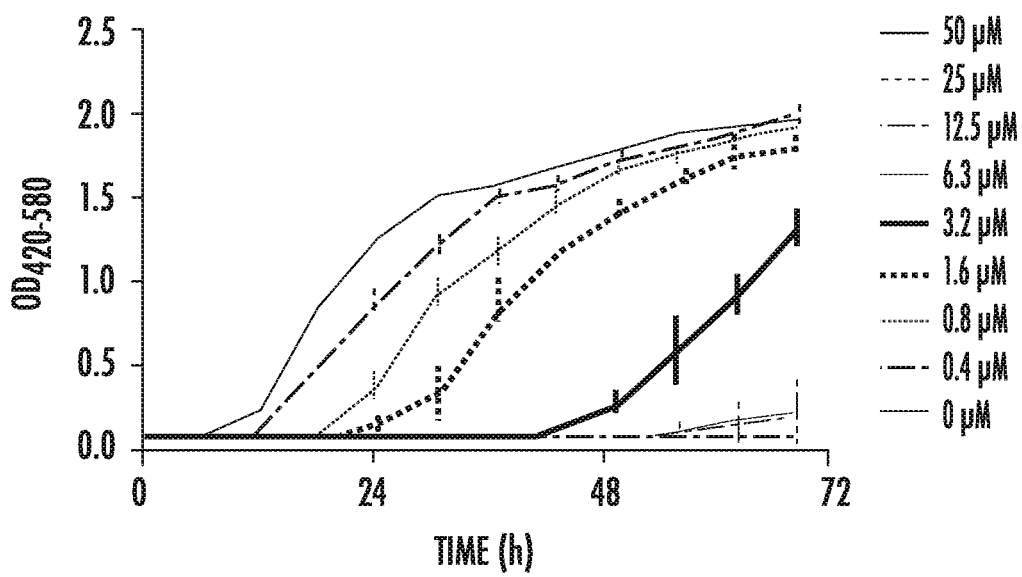
Figure 2E:
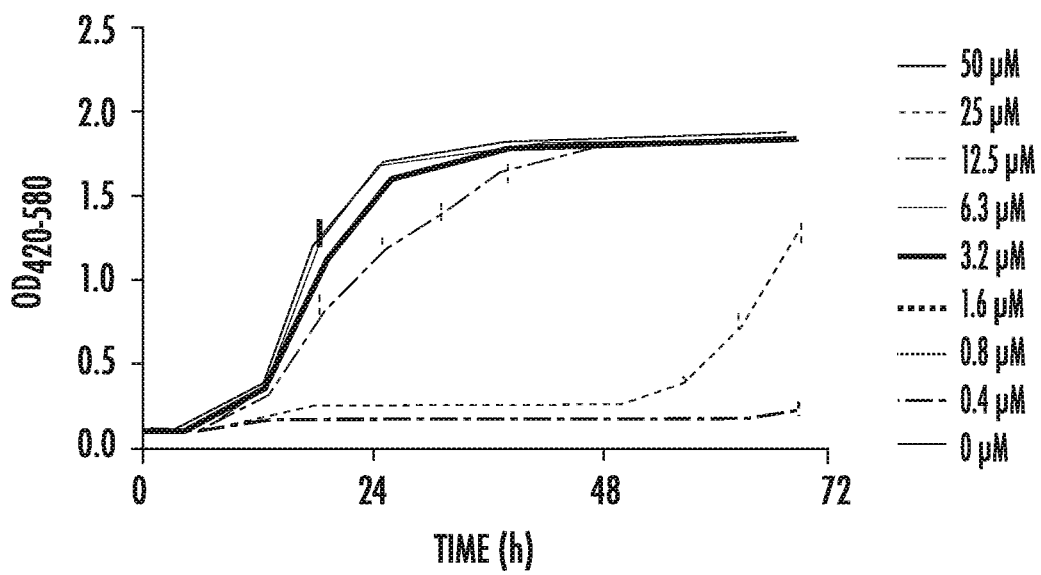
Figure 2F:
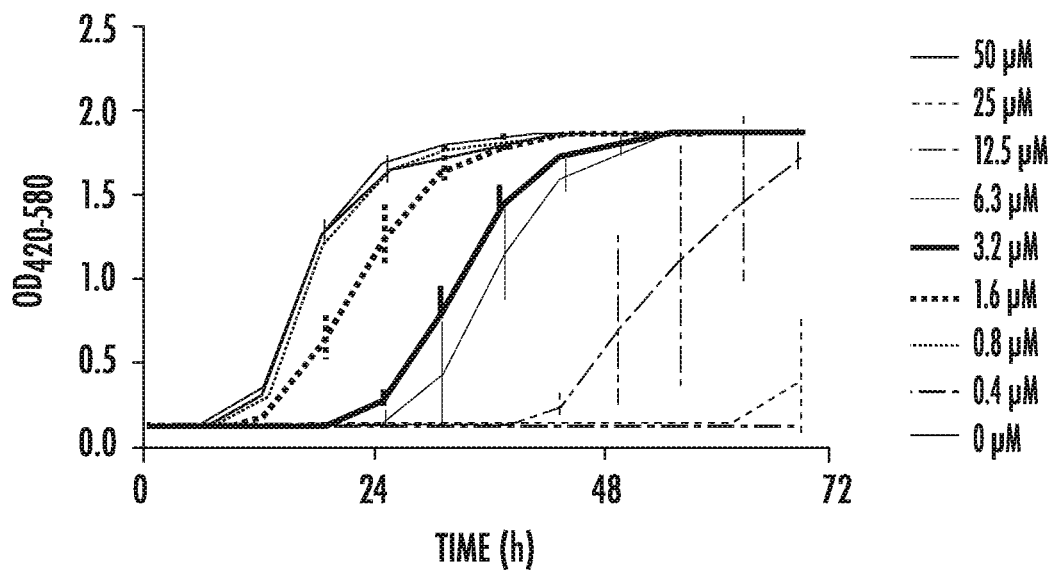
Figure 2G:
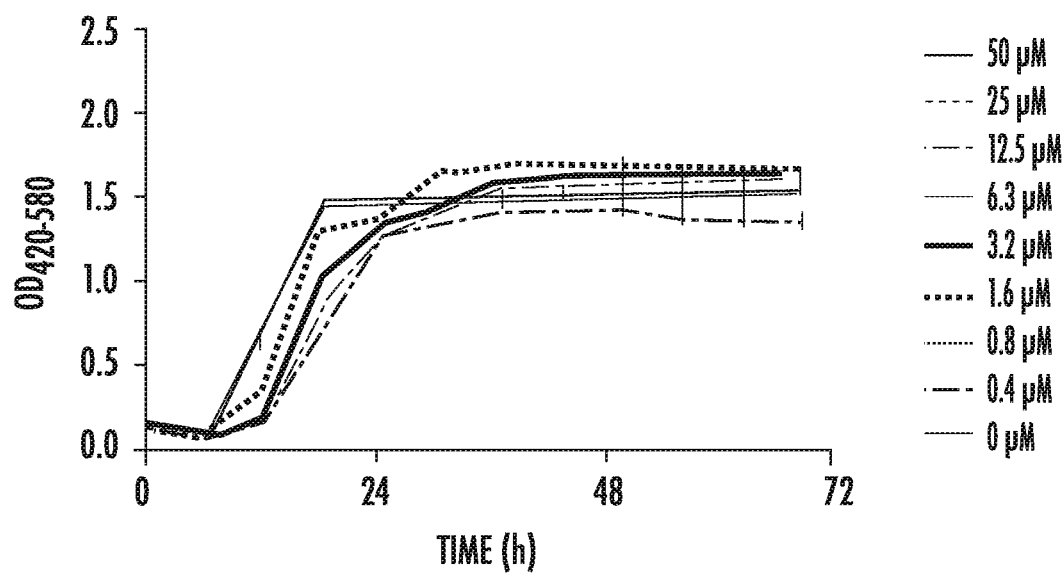
Figure 2H:
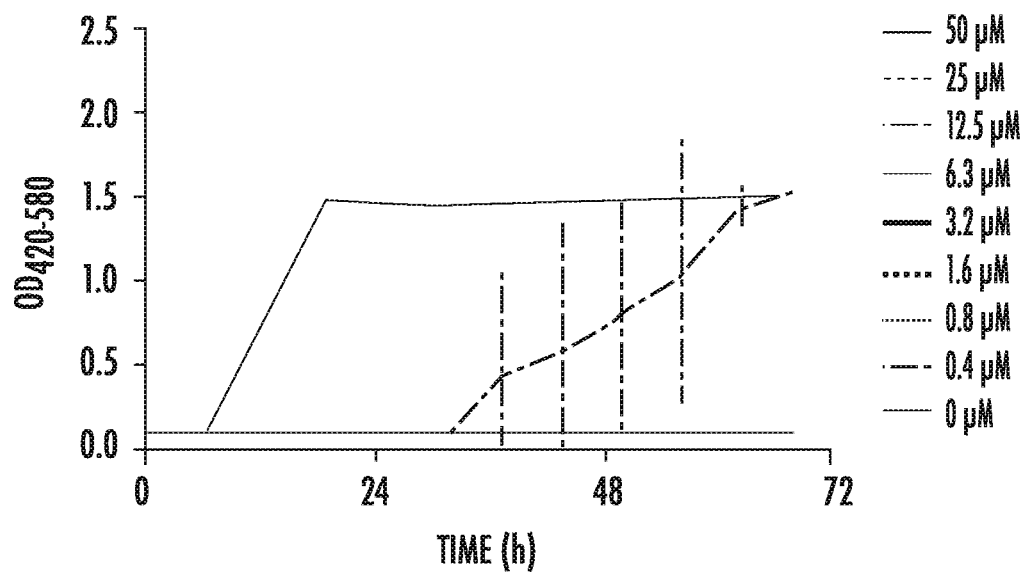

DM262 activity against other fungal species. After identifying DM262 as a potential new antifungal candidate, the inventors investigated the antifungal activity in several other common and uncommon fungal pathogens such as *Lomentospora prolificans* (FIGS. 2C and D), *Cryptococcus gattii* (FIGS. 2E and F) and *Candida albicans* (FIGS. 2G and H). Growth inhibition assays with a 2-fold dilution series of DM262 in *L. prolificans* showed complete resistance to fluconazole even at the highest concentration we tested, 50 µM. DM262 treatment was fungistatic at a concentration of 50 to 12.5 µM and growth was delayed at 3.2 µM down to 0.39 µM. *Cryptococcus gattii* in the same assay showed resistance to fluconazole as growth was unaffected at 6.3 µM and lower. At 12.5 µM and higher of DM262, there was significant delay in the growth of *C. gattii*. Finally, when examining the susceptibility in *Candida albicans* with fluconazole yielded only slight decrease in final $OD_{420-580}$. The minimum inhibitory concentrations (MIC) has been compared for all the fungal pathogens studied here for fluconazole and DM262 (Table 2). The *L. prolificans* and *C. albicans* strains studied were classified as resistant against fluconazole as there was no fungicidal concentration up to 50 µM, the highest concentration we studied (Table 2).

Table 2. Minimum inhibitory concentration (MIC) results. The inventors measured the minimum inhibitory concentration after 72 h of fluconazole versus DM262 in four different fungal species: *C. neoformans, L. prolificans, C. gattii* and *C. albicans*. "Res" denotes resistance to the highest concentration of drug we analyzed, 50 µM.

TABLE 2

MIC results by fungal species

|  | Fluconazole | DM262 |
|---|---|---|
| C. neoformans | 25 µM | 0.8 µM |
| L. prolificans | Res | 6.3 µM |
| C. gattii | 50 µM | 50 µM |
| C. albicans | Res | 0.8 µM |

Figure 3:
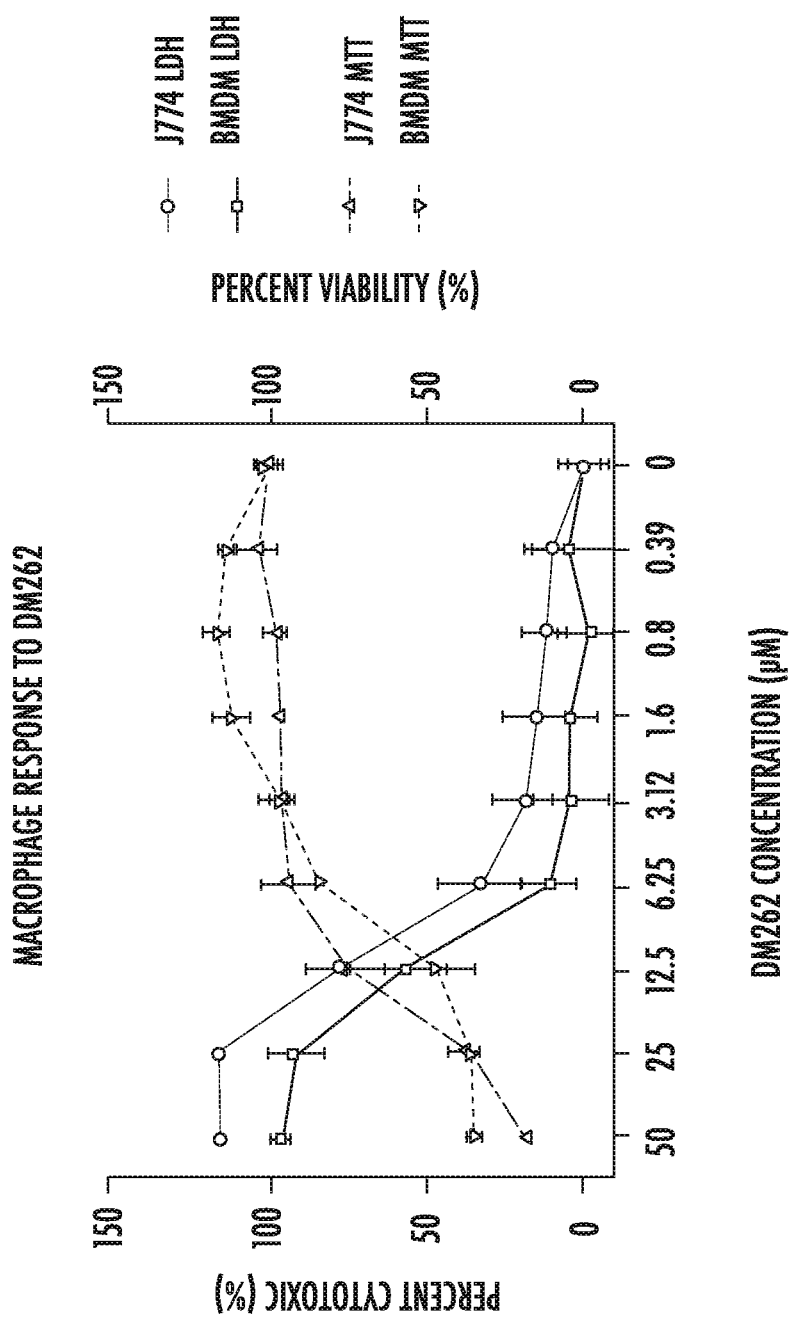
FIG. 3. Mammalian cell cytotoxicity. A) Viability was measured in BMDM cells using MTT assay comparing fluconazole to C262 which is shown to have an $LD_{50}$ of 50 μM. B) Cell lysis was measured by LDH release into the supernatant of BMDMs showing similar numbers with an $LD_{50}$ of 50 μM. Experiments were performed in triplicate. Shown is mean and standard deviation for each value.

Mammalian cell toxicity. To investigate the effects DM262 had on host mammalian cells, we examined cytotoxic lysis and viability in murine bone marrow derived macrophages (BMDM) by measuring lactate dehydrogenase (LDH) and metabolism (MTT). Both assays yielded similar $LD_{50}$ values of 50 µM for DM262 and with minimal variance from DMSO vehicle control up to 12.5 µM (FIG. 3).

Figure 4A:
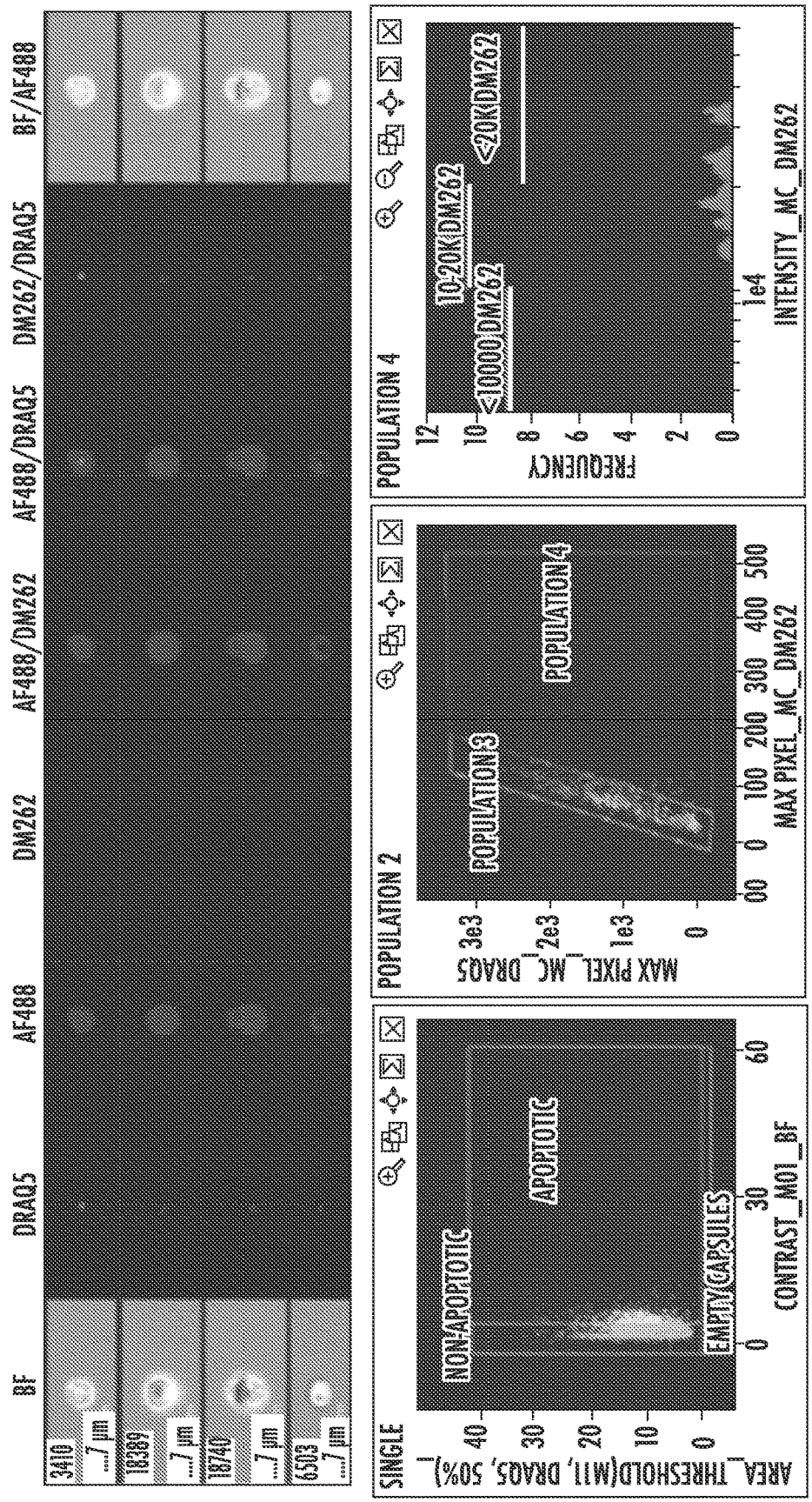
FIG. 4A-4D. Internalization of DM262 in *C. neoformans*. Two populations of cryptococcal cells were treated with either DMSO (A) or 50 μM DM262 (B) for 24 h prior to fixing and analysis on an Amnis ImageStream MKII. DRAQ5 stained nuclei (red) and AF488 (green) stained 18B7 conjugated to the polysaccharide capsule of *C. neoformans* outlining the exterior of the cell. DM262 appears to associate with the nuclei in our investigation. Representative plots from ImageStream analysis highlighting the main differences between untreated and treated cells are below each sample. A complete analysis of all concentrations is available as Supplemental Material S5 (C) Emission scan of *C. neoformans* cells exposed to DM262 at various concentrations. (D) Dose-dependent plot at optimal excitation and emission wavelength for DM262. Cells were previously washed twice in PBS to remove any residual DM262 in the media. Fluorescence of control cells +/−DMSO are shown in green bars.
Figure 4B:
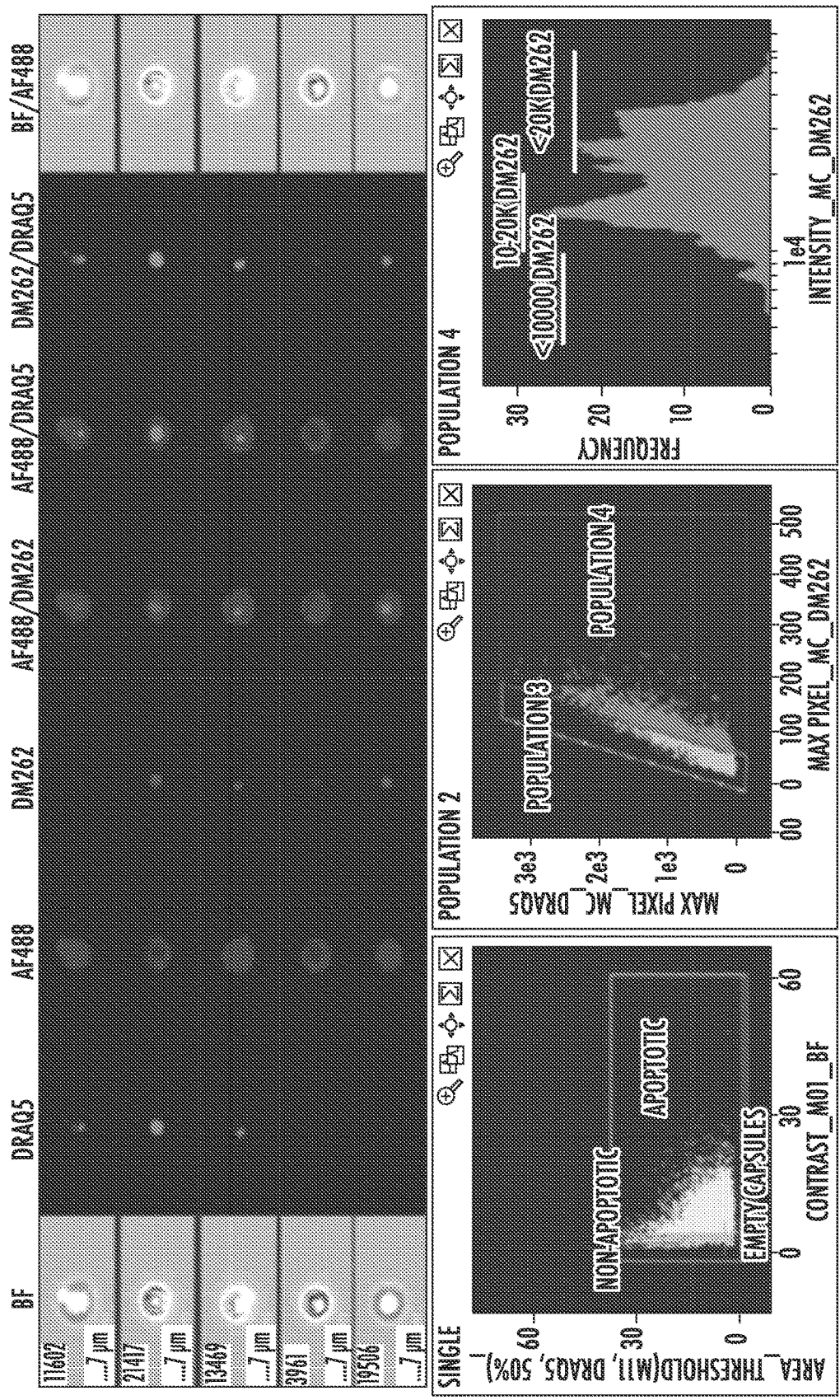
Figure 4C:
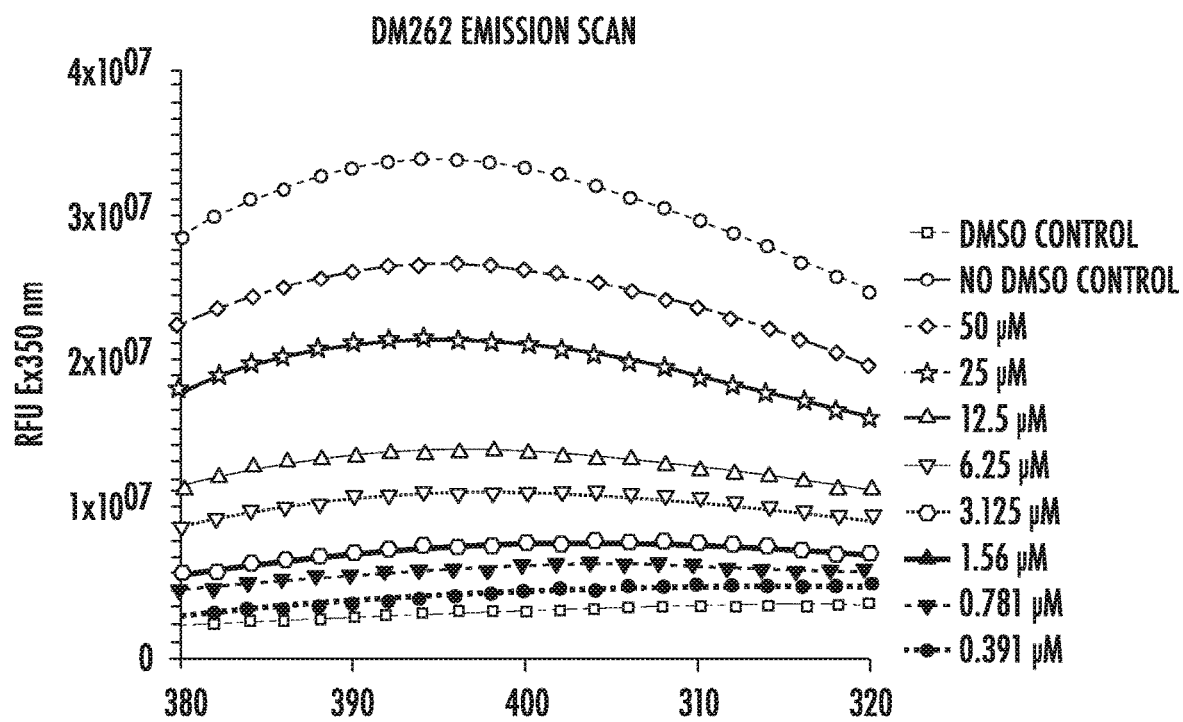
Figure 4D:
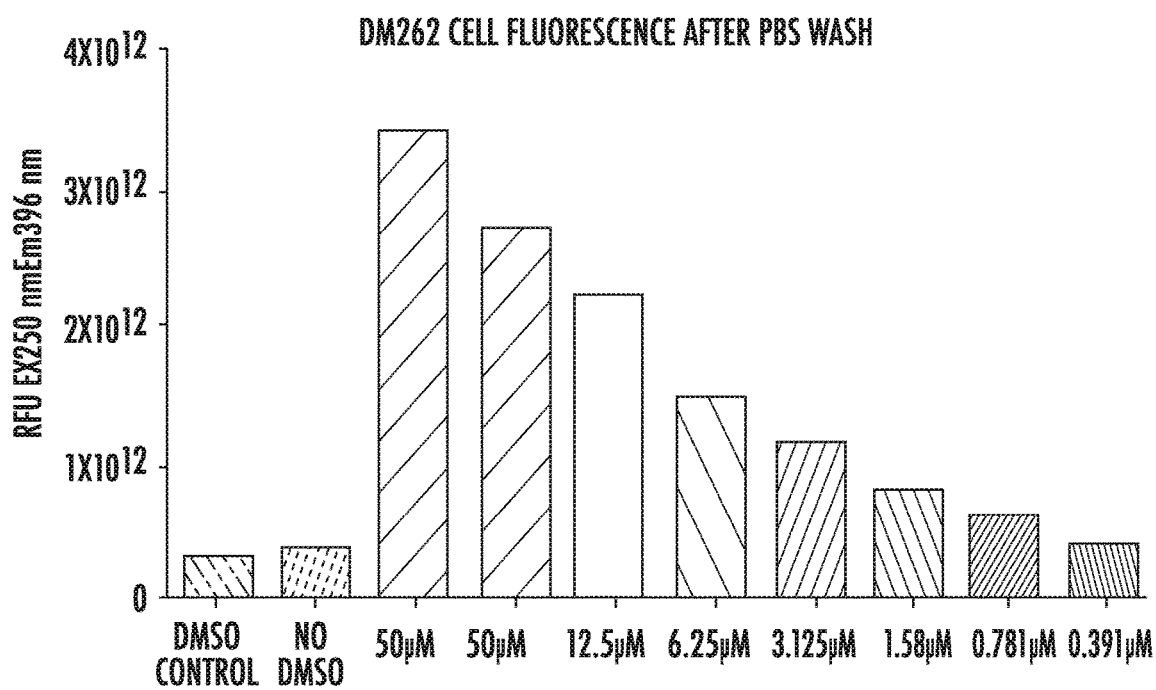
Figure 5A:
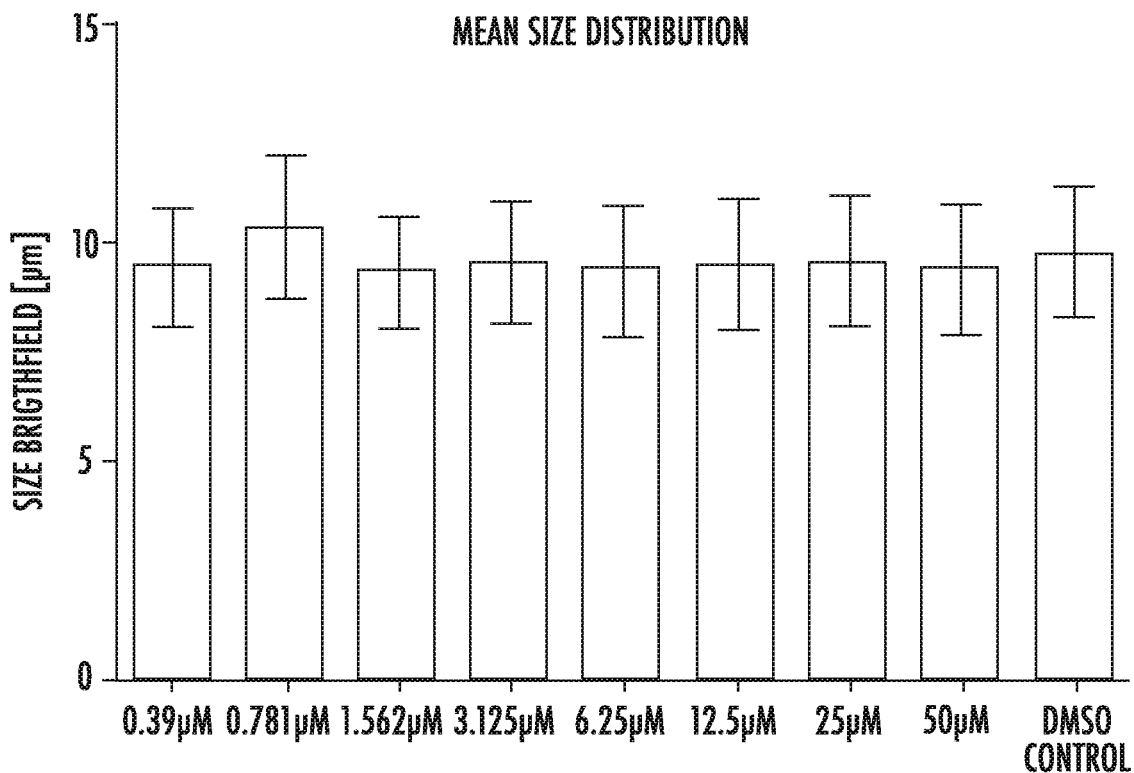
FIG. 5A-5B. Morphological characteristics of DM262 treated *C. neoformans* cells.
Figure 5B:
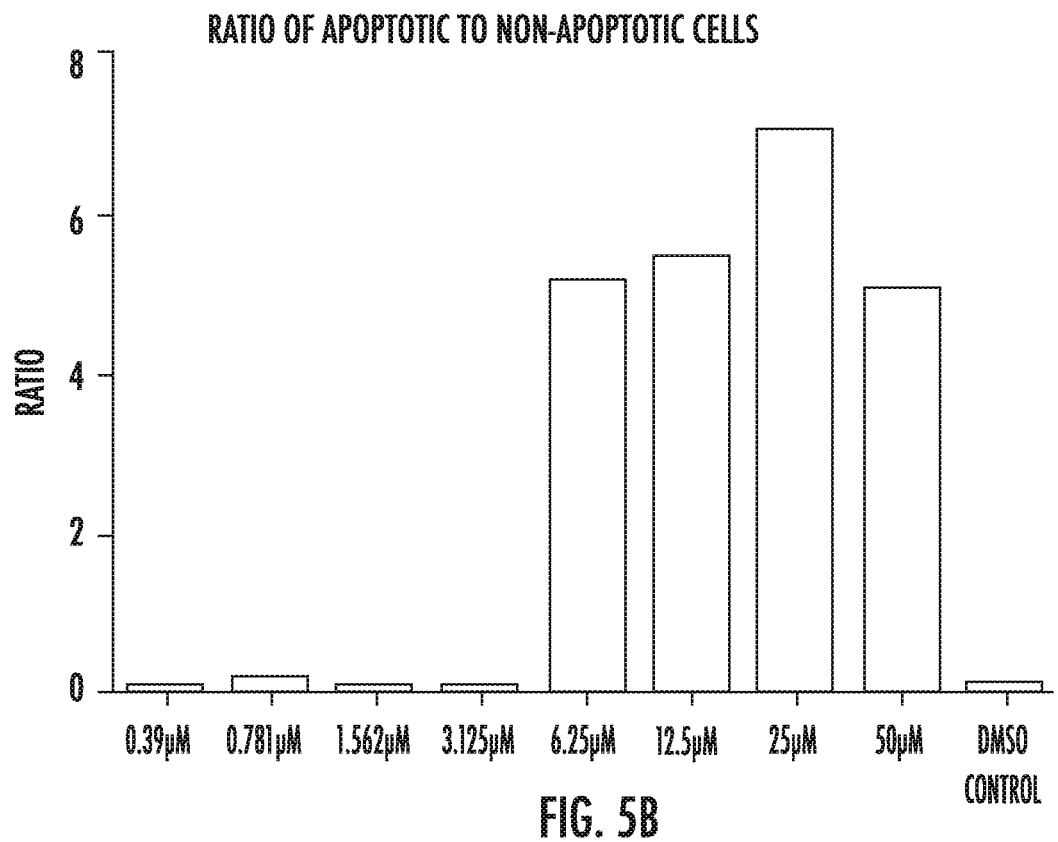

Internalization of DM262. To determine where the drug acts on *C. neoformans*, the utilized imaging flow cytometry in combination with fluorescence detection of DM262 as well as immunostaining with a capsule-specific mAB detected via an Alexa Fluor 488 secondary antibody (FIG. 4A, B, Supplemental Material S3, S4). The inventors determined through an emission and excitation scan the optimal conditions for DM262 detection via fluorescence using a range of concentrations. The optimal excitation of DM262 was achieved at 360 nm and the maximum emission wavelength was determined to be at 396 nm (FIG. 4C). Although not at an optimal excitation wavelength, by using the 405-nm laser of the Amnis ImageStream the inventors were able to detect a dose-dependent fluorescence of DM262 within *C. neoformans* and not within the capsule. Furthermore, we were unable to washout DM262 from the cells once incubated with the drug. DM262 treated cryptococcal cells in the range from 50 µM-1.56 µM were seen colocalizing with the nuclei using the 405-nm laser while we were unable to detect a signal in the DMSO treated sample (FIG. 4A). A dose-dependent increase in DM262 fluorescence was observed using either the ImageStream analysis or a SpectraMax IX3 plate reader using optimal excitation and emission wavelengths (FIG. 4D). Treatment of *C. neoformans* with DM262 had no effect on the average size of the cells (FIG. 5A), however based on morphological parameters in particular shape and size of the nucleus an apoptotic index was calculated with IDEAS 6.2, indicating that at a concentration of 6.25 µM cells were dramatically trending towards apoptosis (FIG. 5B). Further studies will be required to identify the potential protein targets of DM262.

Potential antifungal therapy identified in this study may be added to the arsenal currently available to healthcare professionals to aid patients. The Malaria Box was an invaluable tool, kindly distributed by the Medicines for Malaria Venture with the hopes of identifying novel uses for drugs that have previously been identified as candidate therapies. The inventors have shown that DM262 has significant antifungal activity in two of the most common fungal species, *C. neoformans* and *C. albicans*, as well as against two uncommon fungal species *Lomentospora pro-*

*lificans* and *Cryptococcus gattii* that cause problems via debilitating cutaneous infections or fatal pneumonia in immunocompetent patients. While the reflection of DM262 efficiency against *C. gattii* appears to be comparable at 72 h treatment to fluconazole (Table 2), there is a severe delay in growth with DM262 according to the growth curves. DM262 at 12.5 µM treatment does not reach log phase until approximately 48 h while the same treatment of fluconazole shows only a slight shift in log phase growth (FIGS. 2E and F—gray bar). A combination therapy approach with DM262 might lead to a successful fungicidal activity since most likely a different molecular target is engaged in its inhibitory activity.

There is some room for improvement of this compound by modifying the unreactive aniline groups of DM262 for increased solubility and more efficient delivery. While the oral bioavailability is currently unknown for DM262, intravenous systemic delivery is still viable despite its solubility profile.

In this study, the inventors have identified a potential new antifungal drug, DM262. The next step in the development of this novel drug is to identify its target pathway. The ability to visualize DM262 fluorescence will allow us to more easily identify a potential target pathway. With a target identified, the inventors may be able to modify the compound to increase specificity in order to decrease toxicity and off-target inhibition.

Embodiments of the disclosure concern methods and/or compositions for treating and/or preventing a fungal infection in which modulation of autophagy may be directly or indirectly related, most preferably the inhibition of fungal autophagy. In certain embodiments, subjects, such as humans, with a fungal infection such as *C. neoformans, L. prolificans, C. gattii* and *C. albicans*, as examples, may be treated with one or more of the compositions described in Table 1 or a compound of Formula I, II, III, or a combination thereof.

In certain embodiments, the level to which an inhibitor is able to decrease fungal growth may be any level so long as it provides amelioration of at least one symptom of the fungal infection. The level of fungal growth may decrease by at least 2, 3, 4, 5, 10, 25, 50, 100, 1000, or more fold expression compared to the level of fungal growth in a standard (a subject not administered a compound of Formula I, II, or III) in at least some cases. An individual may monitor fungal growth (or inhibition levels) by methods provided in the Methods/Example section of this patent application.

An individual known to have a fungal infection, suspected of having a fungal infection, or at risk for having a fungal infection may be provided an effective amount of a composition of the present, including one or more compounds listed in Table 1 or a compound of Formula I, II, III, or a combination thereof. Those at risk for a fungal infection may be those individuals having one or more genetic factors, may be of advancing age, may have an immune deficiency, and/or may have a family history, for example.

In particular embodiments of the disclosure, an individual is given an agent for antifungal therapy in addition to the one or more of the compositions of the present inventions. Such additional therapy may include amphotericin B, flucytosine, fluconazole, itraconazole, ketoconazole, miconazole and voriconazole, or a combination, for example. When combination therapy is employed with one or more compositions of the present invention, the additional therapy may be given prior to, at the same time as, and/or subsequent to the composition of the present invention.

Certain methods of the disclosure provide for methods of diagnosing fungal infection prior to the therapeutic methods of the disclosure, and such diagnosis may occur by any methods or means currently available.

Pharmaceutical Preparations

Pharmaceutical compositions of the present invention comprise an effective amount of one or more of the compounds in Table 1 or a compound of Formula I, II, III, or a combination thereof, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one composition of the present invention or additional active ingredient will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The compositions of the present invention may comprise different types of carriers depending on whether it is to be administered in solid, liquid or aerosol form, and whether it need to be sterile for such routes of administration as injection. The present compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The compounds, or compositions of the present invention, including a compound of Formula I, II, III, or a combination thereof, may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. In accordance with the present invention, a composition of the present inventions is combined with the carrier in any convenient and practical manner, i.e., by solution, suspension, emulsification, admixture, encapsulation, absorption and the like. Such procedures are routine for those skilled in the art.

In a specific embodiment of the present invention, a composition, or compound of the present invention, is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include a composition of the present invention, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition of the present invention in a lipid vehicle. For example, an inhibitor of fungal autophagy may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient may be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions including a compound of Formula I, II, III, or a combination thereof, may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In one embodiment of the present disclosure, the antifungal compositions of the present invention including a compound of Formula I, II, III, or a combination thereof, are formulated to be administered via an alimentary route.

Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure, including a compound of Formula I, II, III, or a combination thereof, may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, the antifungal compositions of the present invention, including a compound of Formula I, II, III, or a combination thereof, may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneously, or intraperitoneally U.S. Pat. Nos. 6,7537, 514, 6,613,308, 5,466,468, 5,543,158; 5,641,515; and 5,399, 363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active antifungal compound, including a compound of Formula I, II, III, or a combination thereof, may be formulated for administration via various miscellaneous routes, for example, topical (i.e., transdermal) administration, mucosal administration (intranasal, vaginal, etc.) and/or inhalation. Pharmaceutical compositions for topical administration may include the active compound formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions including a compound of Formula I, II, III, or a combination thereof, may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Kits of the Disclosure

Any of the compositions described herein may be comprised in a kit. In a non-limiting example, an antifungal composition of the present invention, such compound Formula I, II, III, or a combination thereof, may be comprised in a kit. The kits may comprise a suitably aliquoted of a composition of the present invention and, in some cases, one or more additional agents. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing an antifungal composition of the present invention and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. An antifungal composition of the present invention, including a compound of Formula I, II, III, or a combination thereof, may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

Methods/Examples

The following Methods/Examples have been included to provide guidance to one of ordinary skill in the art for practicing representative embodiments of the presently disclosed subject matter. In light of the present disclosure and the general level of skill in the art, those of skill can appreciate that the following Methods/Examples are intended to be exemplary only and that numerous changes, modifications, and alterations can be employed without departing from the scope of the presently disclosed subject matter. The following Methods/Examples are offered by way of illustration and not by way of limitation.

Materials and Methods

Strains. H99 (Serotype A) is a well-characterized wild type laboratory reference strain of *Cryptococcus neoformans* (22). H99 was selected because it is a virulent strain widely by the field. *Cryptococcus gattii* strain R265 is used as the primary reference strain to which the genome is based (ATCC MYA-4093). This strain was isolated from the Vancouver Island (British Columbia, Canada) outbreak of 2004 (23, 24). H99 and R265 were maintained in Sabouraud (Sab) dextrose broth at 30° C. with constant 200 RPM agitation. One day prior to each experimental drug treatment, Sab broth was inoculated from glycerol stock and grown overnight to log phase before washing with PBS and resuspending in fresh Sab broth prior to treatment.

The *Lomentospora prolificans* strain we chose is a clinical isolate which is antifungal resistant, from an 11-year old boy in Australia (25) (AMMRL 140.04 Catalogue #90853, ATCC, Manassas, Va., USA). AMMRL was grown on Sab dextrose rich media plates and incubated for (5-7 days) at 30° C. prior to rinsing the surface with PBS to collect conidia for drug treatment dilution series assays.

SC5314 *Candida albicans* is one of the original background strains used in systematic sequencing of the genome (26). It is also a common laboratory strain and virulent in systemic infection of mouse models. *C. albicans* was streaked from frozen glycerol stocks on Sab rich media plates before inoculation in Sab dextrose broth before growing overnight at 30° C. with constant 200 RPM agitation.

Compound library. 400 compounds were made available by the Medicines for Malaria Venture (Geneva, Switzerland) in the form of the open-access MMV Malaria Box. Compounds were stored at −80° C. in 100% DMSO at a concentration of 10 mM. Before usage, compounds were thawed at room temperature and thoroughly mixed. Compounds were diluted in 2-fold series 10 mM down to 0.8 mM with DMSO before subsequent growth inhibition assays.

Growth inhibition assays. The effectiveness of these MMV Malaria Box compounds against *C. neoformans* was measured by turbidity over time. The Bioscreen C™ (Growth Curves USA, Piscataway, N.J.) allows us to analyze ~60 compounds at a time in triplicate with constant temperature and agitation. Assays were measured at 420-580 nm, wideband range every 15' for 72 h at 37° C. to simulate physiologically relevant temperatures. Wideband is generally used for turbidity measurements, as it is mostly insensitive to changes in color. All compounds were suspended in dimethyl sulfoxide (DMSO) and each test run of 60 compounds had an independent set of DMSO vehicle and media alone controls. We inoculated $5 \times 10^3$ H99 *C. neoformans* and SC5314 *C. albicans* in 200 µl of Sabouraud dextrose broth in each of the honeycomb (HC-2) plate's 100 wells. A two-fold dilution series of each compound from 50 µM down to 0.39 µM final concentration were tested for effects against *C. neoformans*. To qualitatively differentiate fungistatic and fungicidal activity, 5 µl of each well after 72 h were spotted on Sabouraud dextrose agar rich media plates and allowed to grow at the optimal temperature 30° C. to induce a full recovery of viable yeast. Spots were noted after 24 h to identify fungicidal versus fungistatic concentrations of each compound. We examined the efficiency of the top five compounds against *C. neoformans* and *C. albicans*.

Mammalian cell viability and toxicity assays. Bone marrow was isolated from 7-14 week-old C57Bl/6 mice and differentiated at 37° C. and 9.5% $CO_2$ for 7 days with bone marrow derived macrophage (BMDM) media consisting of DMEM, 20% L929 conditioned media, 10% FBS, 1% non-essential amino acids, 1% Gibco™ GlutaMAX™ (Thermo Fisher Scientific, Halethorpe, Md.), 1% HEPES, 1% pen-strep, and 0.1% β-mercaptoethanol. $5 \times 10^4$ BMDM cells were plated in 200 µl/well in a 96-well format. For the MTT colorimetric assay, thiazolyl blue tetrazolium bromide (Sigma, M2128) was added to cells where it is reduced into pigmented formazan crystals by viable mammalian cells. Cells were incubated for 2 h to metabolize the tetrazolium salts before lysing with extraction buffer (12.5% SDS and 45% DMF) overnight. The following day, absorbance was measured at 570 nm in an EMax Plus Microplate Reader (Molecular Devices, California, USA).

Measuring lactate dehydrogenase (LDH), a stable cytoplasmic enzyme, gives an indication of lysis and cell death versus cell viability from MTT. CytoTox 96® Non-Radioactive Cytotoxicity Assay (Promega, G1781) was used to measure the lytic release of LDH. After 2 h exposure of compound, supernatant is removed and incubated with substrate and assay buffer for 30 m before acetic acid is added as a stop solution. Absorbance was measured at 570 nm in an EMax Plus Microplate Reader.

Fluorescence of DM262. We assessed the fluorescence of 1M DM262 and DMSO vehicle control alone, using the Fluorilog-3 (Horiba Jobin Yvon). To identify the optimal excitation wavelength, we did a broad-spectrum excitation scan of every odd wavelength between 300 and 500 nm which showed 391-393 nm as the optimum excitation wavelength (Supplemental Material 51). Subsequently, we excited at 340 nm and scanned between 355 and 500 nm for optimal emission wavelengths.

Imaging flow cytometry on *C. neoformans*. Cultures of *C. neoformans* were grown in liquid medium under optimum conditions (200 rpm, 30° C.) in the presence of DM262 ranging from 50 µM to 0.39 µM with a final DMSO concentration of 0.5% in the culture as well as a control culture with 0.5% DMSO for 24 h. Cultures were harvested and washed twice with ice-cold 1×PBS to remove media components as well as DM262 remaining in the culture media. Samples for Amnis ImageStream$^X$ MK II (Amnis Cooperation, Seattle, Wash.) analysis were fixed with freshly prepared 4% Paraformaldehyde for 40 minutes under constant rotation at room temperature. Each sample was split into two where one was stained with 18B7, a monoclonal antibody specific for the polysaccharide capsule (27), while DRAQ5 was utilized for the nuclear stain. The second sample was kept unstained to be able to detect cellular auto-fluorescence as well as fluorescence of DM262. The untreated DMSO vehicle control was used to generate a compensation matrix correcting for the intrinsic auto fluorescence of the cells. Event counts were based on the area in the bright-field channel being greater than 12 to collect all cells (single and multiple). The instrument was set to a magnification of 60× with extended depth of field (EDF) turned on and all lasers at their maximum power except for the side-scatter laser (405 nm 90 mW, 488 nm 100 mM, 658 nm 120 mW, 768 nm 3.25 mW) 25000 events were collected per sample and subsequently analyzed using identical gates with IDEAS 6.2.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of using a compound of Formula I to treat a fungal infection in a subject comprising the steps of: administering an effective amount of a compound of Formula I to a subject having or suspected of having a fungal infection wherein the compound of Formula I is:

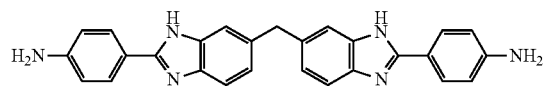 [SMILES: Nc1ccc(-c2nc3ccc(Cc4ccc5nc(-c6ccc(N)cc6)[nH]c5c4)cc3[nH]2)cc1]

a pharmaceutically acceptable salt, solvate, or stereoisomer thereof, wherein the fungal infection is selected from the group consisting of *C. neoformans, C. gattii, L. prolificans, C. albicans*, or a combination thereof.

2. The method of claim 1 wherein the compound of Formula I is administered to the subject as a pharmaceutical composition comprising a compound of Formula I and a pharmaceutically acceptable carrier.

3. The method of claim 1 wherein the compound of Formula I is administered to the subject topically.

4. The method of claim 1 wherein the subject is a human.

5. The method of claim 1 further comprising the step of administering an antifungal agent to the subject.

6. The method of claim 5 wherein the antifungal agent is selected from the group consisting of amphotericin B, flucytosine, fluconazole, itraconazole, ketoconazole, miconazole and voriconazole, or a combination thereof.

7. A method of for treating a fungal infection in a subject comprising administering and effective amount of a compound of Formula III,

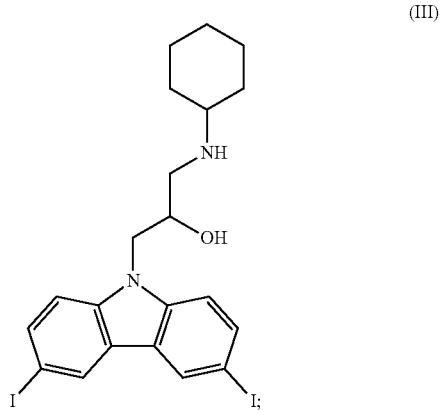 [SMILES: OC(CNC1CCCCC1)Cn1c2ccc(I)cc2c2cc(I)ccc21]

or a pharmaceutically acceptable salt, solvate, or stereoisomer thereof to the subject, wherein the fungal infection is of *C. neoformans*.

8. The method of claim 7 wherein the compound of Formula III III is administered to the subject as a pharmaceutical composition comprising a compound of Formula III and a pharmaceutically acceptable carrier.

9. The method of claim 7 wherein the subject is a human.

10. The method of claim 7 further comprising the step of administering an antifungal agent to the subject.

11. The method of claim 10 wherein the antifungal agent is selected from the group consisting of amphotericin B, flucytosine, fluconazole, itraconazole, ketoconazole, miconazole and voriconazole, or a combination thereof.

12. The method of claim 7 wherein the pharmaceutical composition is administered topically.

* * * * *